(12) United States Patent
Takeuchi et al.

(10) Patent No.: US 6,676,258 B2
(45) Date of Patent: Jan. 13, 2004

(54) EYE CHARACTERISTIC MEASUREMENT APPARATUS WITH SPECKLE NOISE REDUCTION

(75) Inventors: Gaku Takeuchi, Tokyo (JP); Naoki Nakazawa, Tokyo (JP); Masahiro Shibutani, Tokyo (JP); Katsuhiko Kobayashi, Tokyo (JP)

(73) Assignee: Kabushiki Kaisha Topcon (JP)

( * ) Notice: Subject to any disclaimer, the term of this patent is extended or adjusted under 35 U.S.C. 154(b) by 0 days.

(21) Appl. No.: 09/872,538

(22) Filed: Jun. 1, 2001

(65) Prior Publication Data

US 2002/0063849 A1 May 30, 2002

(30) Foreign Application Priority Data

Jun. 2, 2000 (JP) ........................................ 2000-166767

(51) Int. Cl.[7] ................................................. A61B 3/10
(52) U.S. Cl. ...................................................... 351/211
(58) Field of Search ................................ 351/200, 204, 351/205, 206, 209, 210, 211, 221; 600/558; 359/559, 196, 197, 209, 211, 212–215

(56) References Cited

U.S. PATENT DOCUMENTS

| | | | | | |
|---|---|---|---|---|---|
| 4,125,320 A | * | 11/1978 | Rassow et al. | ............. | 351/211 |
| 4,410,244 A | * | 10/1983 | Remijan | ..................... | 351/211 |
| 5,479,221 A | * | 12/1995 | Heine et al. | ................. | 351/211 |
| 5,579,161 A | * | 11/1996 | Sekiguchi | ................... | 359/559 |
| 5,729,374 A | * | 3/1998 | Tiszauer et al. | ............ | 359/212 |
| 5,929,970 A | * | 7/1999 | Mihashi | ...................... | 351/205 |

* cited by examiner

Primary Examiner—George Manuel
Assistant Examiner—John R Sanders
(74) Attorney, Agent, or Firm—Baker Botts LLP

(57) ABSTRACT

The invention provides an apparatus which detects light quantity distribution characteristics of a measuring target image projected to a fundus of an eye to be inspected and measures eye optical characteristics from the light quantity distribution characteristics. A projecting optical system has a light source and projects a measurement target to a fundus of an eye to be inspected by bundle of rays emitted from the light source, and a light receiving optical system condenses the bundle of rays reflected from the fundus of the eye. A photoelectric detector detects light quantity distribution characteristics of an image formed by the light receiving optical system, and an arithmetic unit measures eye optical characteristics of the eye based on a signal output from the photoelectric detector. A deflecting optical member for deflecting bundle of rays incident into both optical paths of the projecting optical system and the light receiving optical system is arranged so as to be rotatable.

4 Claims, 7 Drawing Sheets

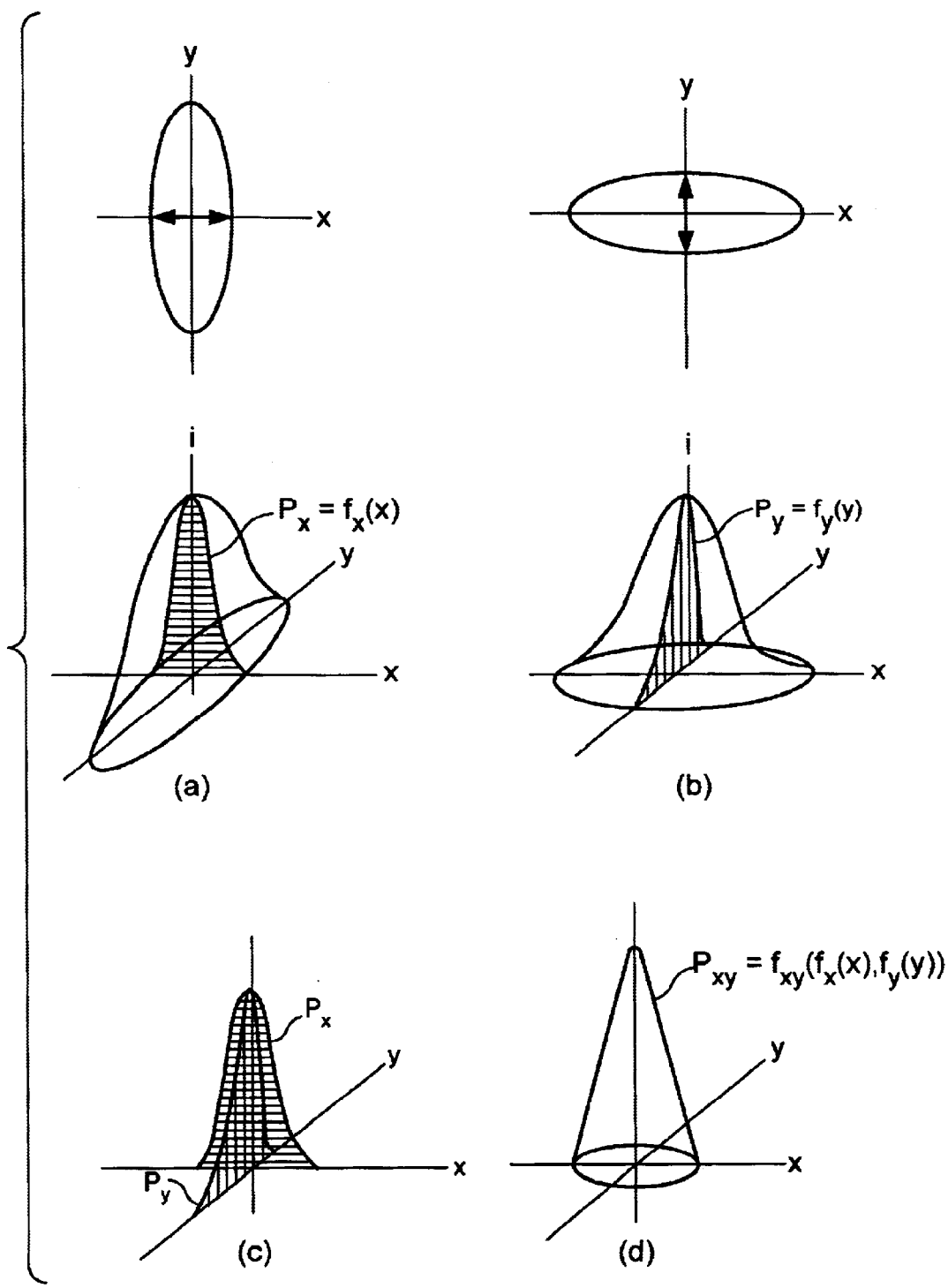
F I G. 5

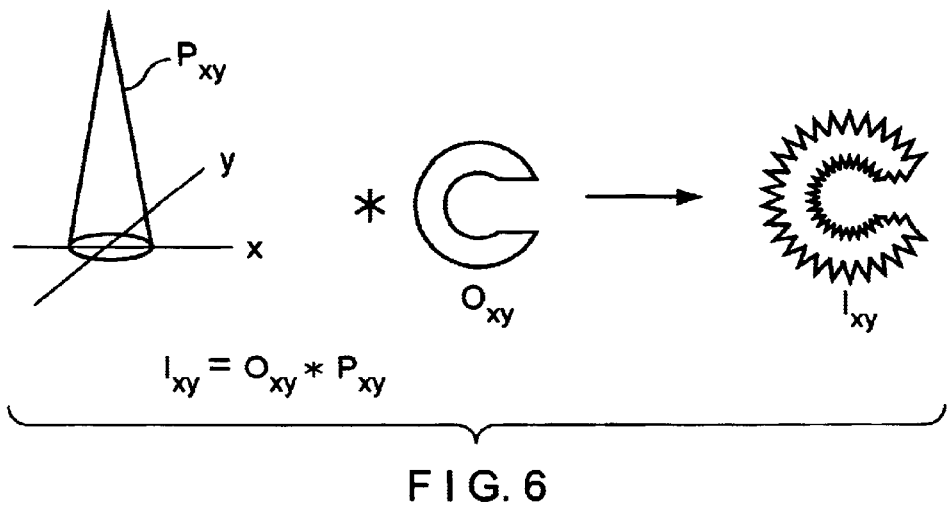
$$I_{xy} = O_{xy} * P_{xy}$$
F I G. 6
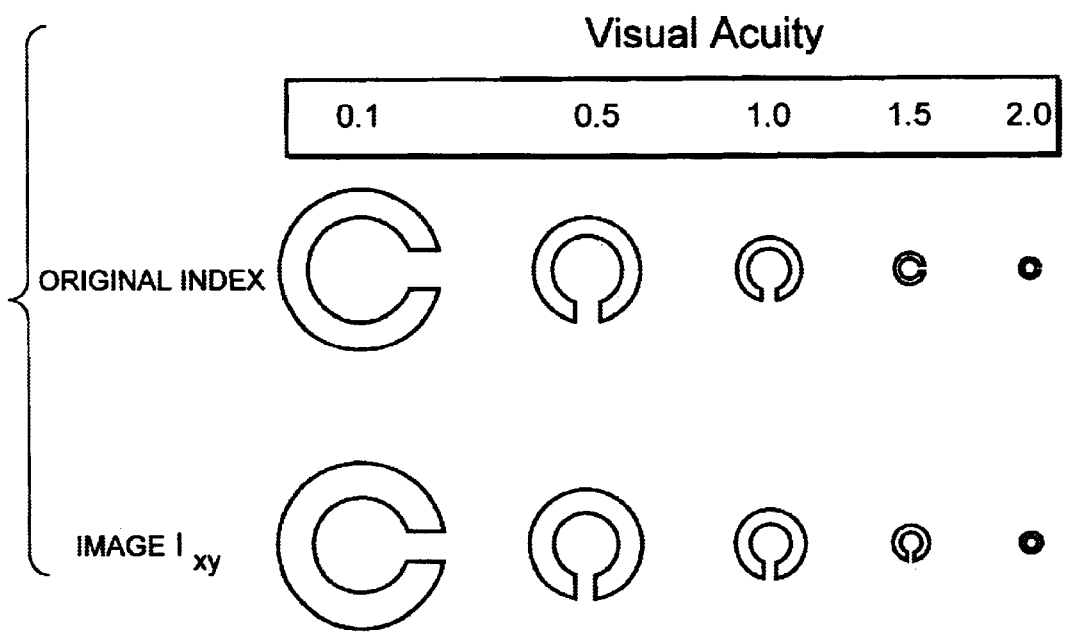
F I G. 7

EYE CHARACTERISTIC MEASUREMENT APPARATUS WITH SPECKLE NOISE REDUCTION

BACKGROUND OF THE INVENTION

The present invention relates to an eye characteristic measuring apparatus where light quantity distribution characteristics of a measuring target image projected to a fundus of an eye to be inspected are detected, and eye optical characteristics are measured from the light quantity distribution characteristics.

In the prior art, an apparatus is known where an illumination image is projected to a fundus of an eye to be inspected, and an image formed by reflected bundle of rays from the fundus of the eye is condensed onto a photoelectric detector, and based on a signal from the photoelectric detector, the light quantity distribution of the reflected image in the fundus (for example, point image light quantity distribution characteristics) is detected, and eye optical characteristics of the eye are measured from the light quantity distribution characteristics detected.

This kind of apparatus is said to desirably use a laser light source or SLD (Super Luminescent Diode) as a light source for bundle of rays projected to a fundus in order to increase the reflected light quantity.

When bundle of rays from such a light source is utilized, however, a speckle noise is inevitably produced to an image formed on the photoelectric detector, and unevenness of the light quantity is produced and the speckle noise becomes obstruction while the light quantity distribution characteristics of the image are measured, resulting in that the measurement cannot be performed with high accuracy.

The present invention intends to solve such problems in the prior art, where a deflection member is rotated and thereby a speckle noise is averaged for an image formed on a light receiving element, and the image can be detected as an image free from the uneven light quantity and the light quantity distribution characteristics can be measured with high accuracy.

SUMMARY OF THE INVENTION

The present invention is in an eye characteristic measuring apparatus for detecting light quantity distribution characteristics of a measurement target image projected to a fundus of an eye to be inspected, and for measuring eye optical characteristics from the light quantity distribution characteristics, where a projecting optical system has a light source and by bundle of rays emitted from the light source, a measurement target is projected to the fundus of the eye, and a light receiving optical system condenses the bundle of rays reflected from the fundus of the eye. A photoelectric detector detects light quantity distribution characteristics of an image formed by the light receiving optical system, and an arithmetic unit measures eye optical characteristics of the fundus of the eye based on a signal output from the photoelectric detector. A deflection optical member is arranged rotatably for deflecting bundle of rays incident into both optical paths of the projecting optical system and the light receiving optical system.

BRIEF DESCRIPTION OF THE DRAWINGS

The accompanying drawings show embodiments of the present invention, in which:

FIGS. 5(*a*)–(*d*) diagramatically illustrate two-dimensional light intensity distributions;

FIG. 6 is a diagram explaining optotype $O_{xy}$ and image $I_{xy}$;

FIG. 7 is a diagram explaining image $I_{xy}$ displayed on display means; and

DESCRIPTION OF THE INVENTION

Figure 1:
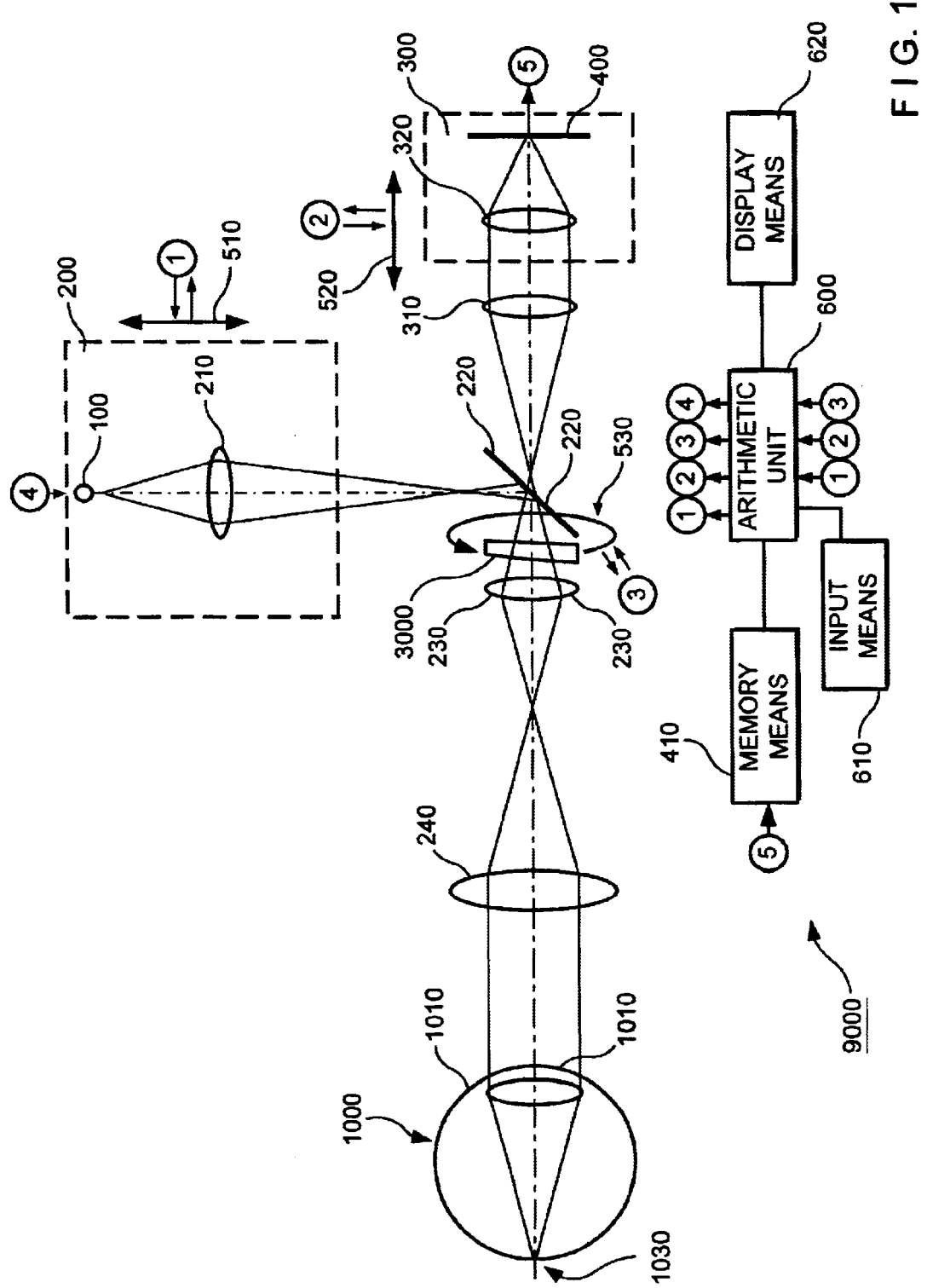
FIG. 1 is a diagram showing the constitution of an eye characteristic measuring apparatus in the embodiment of the invention.

Embodiments of the present invention will be described referring to the accompanying drawings.

An eye characteristic measuring apparatus 9000 in the embodiment includes a projecting optical system 200 having a light source 100 for projecting a measurement target to a fundus of an eye to be inspected by bundle of rays from the light source 100, a light receiving optical system 300 for condensing bundle of rays reflected from the fundus of the eye, a photoelectric detector 400 for detecting the light quantity distribution characteristics of an image formed by the light receiving optical system 300, and an arithmetic unit 600 for estimating optical characteristics of the eye based on a detection signal of the photoelectric detector 400. The eye characteristic measuring apparatus 9000 further includes a deflection prism 3000 for deflecting bundle of rays incident into both optical paths of the projecting optical system 200 and the light receiving optical system 300.

The light source 100 is a point source disposed at the focal position of a projecting lens 210. The light source 100 used in the embodiment is a laser light source with high coherence or an SLD (Super Luminecent Diode) with coherence being not so high as that of the laser light source. In addition, the lighting of the light source 100 is controlled based on the control signal ④ from the arithmetic unit 600.

The projecting optical system 200 is constituted by a projecting lens 210, a beam splitter 220, a relay lens 230 and an objective lens 240.

The projecting lens 210 sends light rays from the light source 100 through the relay lens 230 to the objective lens 240. With the objective lens 240, light rays sent from the projecting lens 210 are made parallel bundle of rays and then are incident to the eye 1000 to be inspected, thereby being focused in the retina 1030 of the eye.

The beam splitter 220 allows the light rays sent from the projecting lens 210 to be directed in the direction of the objective lens 240. The beam splitter 220 allows light rays reflected in the retina 1030 of the eye to transmit.

The light receiving optical system 300 is constituted by the objective lens 210, the relay lens 230, the beam splitter 220, a collimator lens 310 and a focusing lens 320.

The collimator lens 310 allows the light rays transmitting through the beam splitter 220 and reflected in the retina 1030 of the eye to be made parallel bundle of rays and the parallel rays to be sent to the focusing lens 320. With the focusing lens 320, the light rays reflected in the retina 1030 of the eye are focused onto the photoelectric detector 400. The photoelectric detector 400 of the embodiment adopts an image pickup element such as a CCD. The photoelectric detector 400 is not limited to the CCD, but any may be adopted as long as it converts a pickup image into an image signal.

Memory means 410 is a frame memory where the image signal ⑤ from the photoelectric detector 400 is stored.

In addition, the light source 100 is conjugate with the fundus of the eye and in turn the fundus of the eye is conjugate with the photoelectric detector 400.

Projecting lens moving means 510 is a focusing mechanism where the projecting lens 210 is moved and focusing is performed. Similarly, focusing lens driving means 520 is a focusing mechanism where the focusing lens 320 is moved and focusing is performed. In addition, the projecting lens moving means 510 and the focusing lens moving means 520 are provided with moving amount detecting means such as an encoder so that the moving amount of the lens can be detected.

In the present embodiment, a control driving unit is contained where the driving power is supplied to the projecting lens moving means 510 based on the control signal ① output from the arithmetic unit 600. Similarly, in the present embodiment, a control driving unit is contained where the driving power is supplied to the focusing lens driving means 520 based on the control signal ② output from the arithmetic unit 600.

In the present embodiment, although the measurement target projected to the fundus of the eye is a point source image, it may be a slit image or an edge image.

Here the deflection prism 3000 will be explained in detail.

The deflection prism 3000 is a deflection prism of wedge shape made of a light transmitting material, and it is arranged rotatably about the optical axis at a conjugate position, with a pupil of an eye to be inspected, of the shared optical path for the projecting optical system 200 and the light receiving optical system 300. That is, based on the control signal from the arithmetic unit 600, a prism driving unit 530 can rotate the deflection prism 3000. In addition, the deflection prism 3000 corresponds to a deflection optical member.

The deflection prism 3000 is a prism which deflects bundle of rays from the light source 100 very small angle. Main light rays projected to the fundus of the eye to be inspected are deflected very small angle with respect to the position of the pupil of the eye 1000, and the point source image is formed on the fundus of the eye 1000 at the position apart from the center by very small amount. Bundle of rays from the point source again transmit through the deflection prism 3000 and thereby the deflection is reduced, and in the photoelectric detector 400, bundle of rays of the main light rays in parallel to the optical axis are projected.

Here every time an image of one frame is taken from the photoelectric detector 400 to the memory means 410, if the deflection prism 3000 is rotated at a high speed of 10–20 times, the speckle noise is averaged, and the image free from the uneven light quantity is recorded in the memory means 410. Based on the image signal recorded by the memory means 410, the arithmetic unit 600 can calculate the point image intensity distribution of the image.

Although the deflection prism 3000 is arranged within the shared optical path for the projecting optical system 200 and the light receiving optical system 300, the same effects can be obtained also even when the same deflection prisms 3000 are arranged in the respective optical path for the projecting optical system 200 and the light receiving optical system 300 and both deflection prisms 3000 are rotated synchronously.

Here the prism driving unit 530 will be explained.

Figure 8:
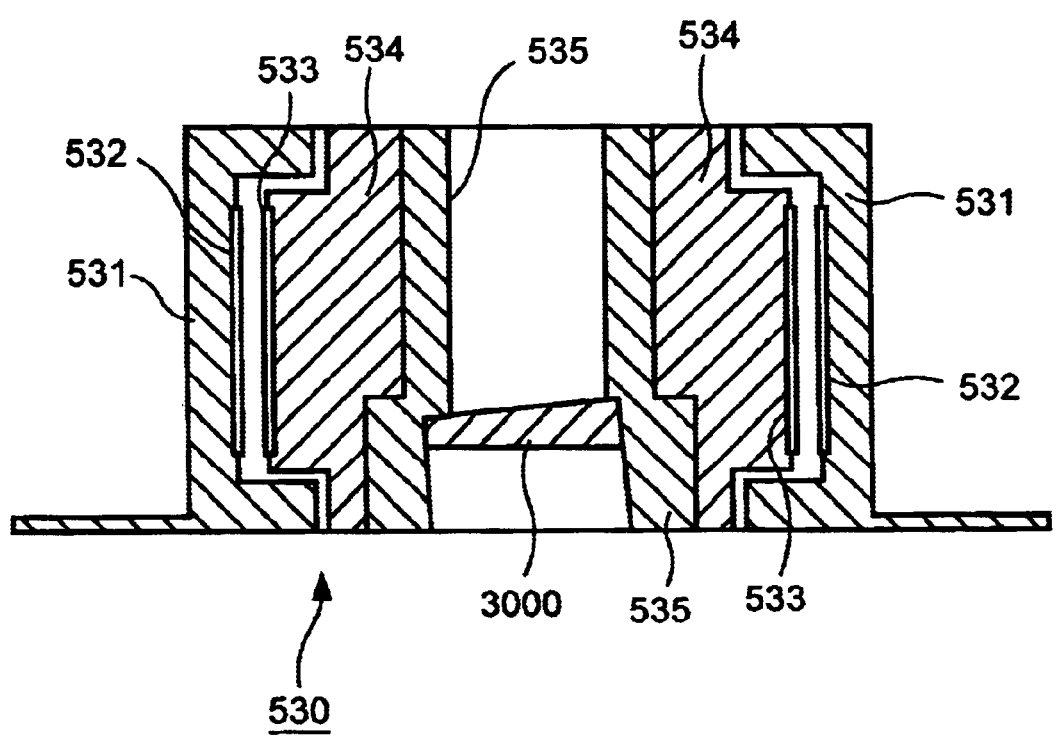
FIG. 8 is a diagram showing the constitution of a prism driving unit.

The prism driving unit 530 of the embodiment, as shown in FIG. 8, is constituted by a hollow motor housing unit 531, a coil 532, a magnet unit 533, a hollow motor rotary unit 534 and a lens cell unit 535.

The deflection prism 3000 is fixed to the lens cell unit 535. Therefore attendant on the rotation of the hollow motor rotary unit 534, the deflection prism 3000 can be rotated at a high speed.

The hollow motor rotary unit 534 is rotatable to the hollow motor housing unit 531, and if the driving power is supplied to the coil 532, the rotation of the deflection prism 3000 can be controlled.

In the present embodiment, a control driving unit is contained for supplying the driving power to the coil 532 based on the control signal ③ output from the arithmetic unit 600. Further a rotary encoder or the like for detecting the rotation of the deflection prism 3000 may be provided.

The arithmetic unit 600 controls the optical characteristic measuring apparatus 9000 as a whole in the embodiment, detects in order the moving amount of the lens by using the projecting lens moving means 510 and the focusing lens driving means 520 and also makes the memory means 410 store the image signal on the photoelectric detector 400 corresponding to the moving position. Based on the moving position of the lens by the projecting lens moving means 410 and the focusing lens driving means 520 and each image signal stored in the memory means 410 corresponding to the moving position, the arithmetic unit 600 performs various sorts of calculation. Further the arithmetic unit 600 controls and drives the prism driving unit 530 and can rotate the deflection prism 3000 at a high speed.

Data and processing instruction are inputted with the input means 610 by the operator. The retina image of the subject to be examined is displayed in the display means 620, where the retina image is calculated and estimated by the optical characteristic measuring apparatus 9000 and is already corrected by the eyeglass lens 90000 actually.

Figure 2:
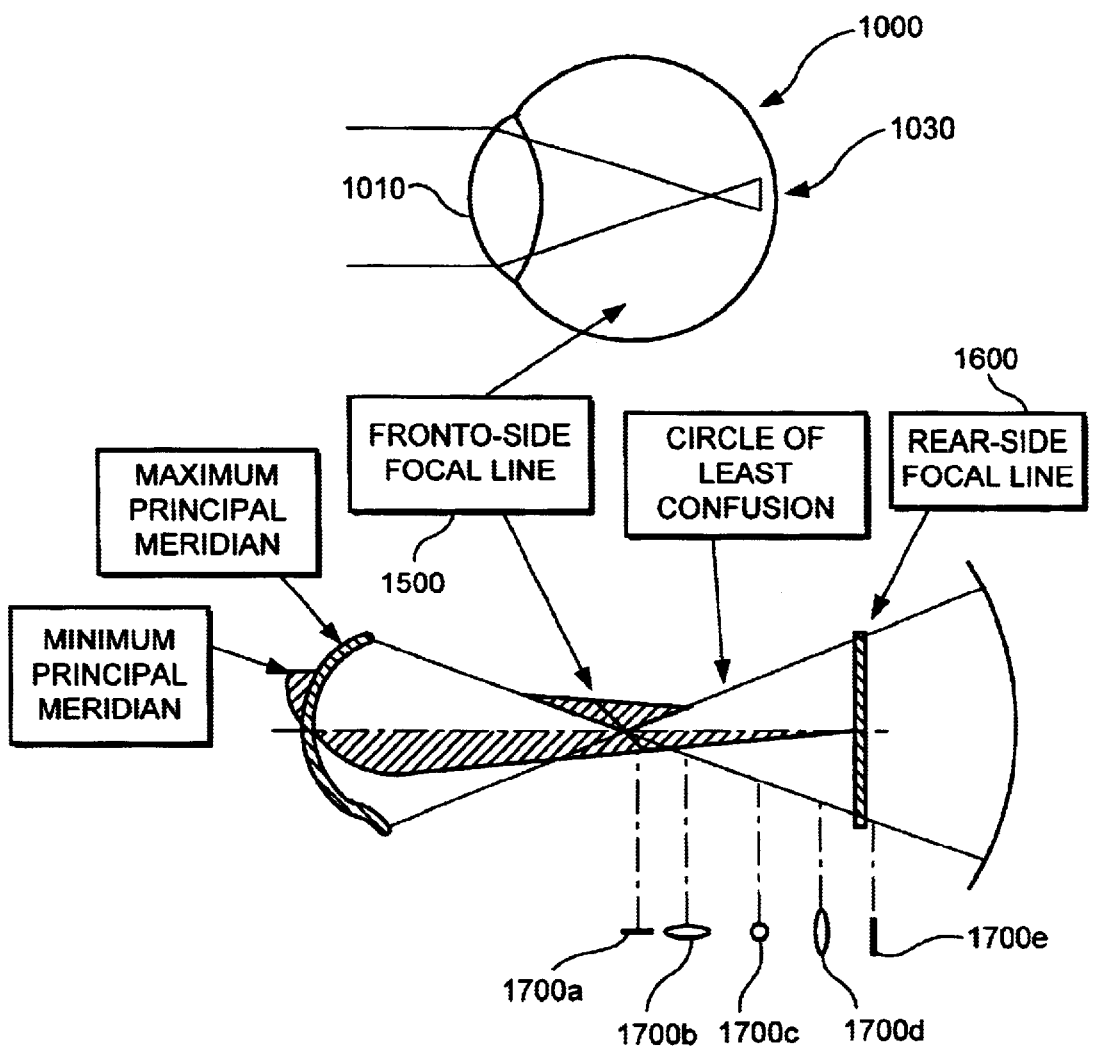
FIG. 2 is a diagram showing schematically the state of bundle of rays when an eye to be inspected is in myopic compound astigmatism.

The procedure for estimating corrected eyesight by using this optical arrangement will be described with respect to a compound myopic astigmatism eye 1000 to be examined, which is shown in FIG. 2. In the case of compound myopic astigmatism, the curvature of the front of the cornea 1010 in the vertical direction and the curvature of the front of the cornea 1010 in the horizontal direction with respect to incident parallel light rays are different from each other, as shown in FIG. 2. Therefore, optical astigmatism or so-called distorted vision is caused.

Because of the astigmatism, the focal point is not present. Instead, there are a front-side focal line 1500, a rear-side focal line 1600, and circles of least confusion (also called focal circles) 1700*a*, 1700*b*, 1700*c* . . . at positions where the light rays becomes smallest in the middle of the front-side focal line 1500 and the rear-side focal line 1600.

Compound myopic astigmatism is characterized in that the curvature of the front of the cornea 1010 in the vertical direction is stronger than the curvature of the front of the cornea 1010 in the horizontal direction, and the front-side focal line 1500 and the rear-side focal line 1600 are both present on the front side of the retina 1030.

Figure 3:
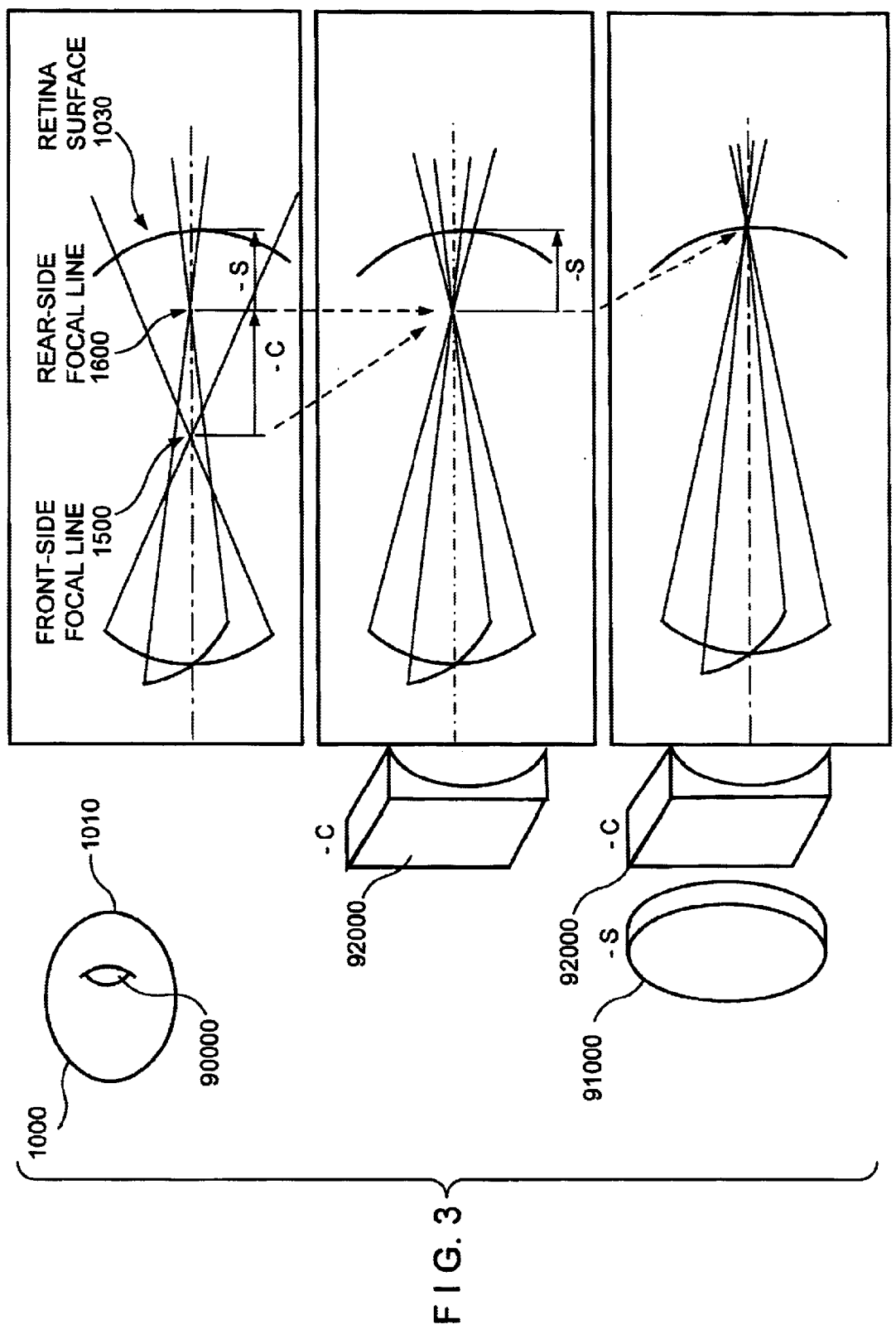
FIG. 3 is a diagram explaining the principle of correction of astigmatism by glasses.

When the eye 1000 to be examined is corrected by an eyeglass lens 90000, the correction is performed, as shown in FIG. 3, by using a spherical lens 91000 with a refractive power of −S diopters and a concave lens 92000 with a refractive power of −C diopters and with its axes aligned with the maximum principal meridian and the minimum principal meridian.

Eyeground image of the front-side focal line 1500, the rear-side focal line 1600, and the circles of least confusion 1700a, 1700b, 1700c . . . can be obtained by moving the projecting lens 210 and the focusing lens 320 shown in FIG. 1. The eyeground images are captured by the photoelectric detector 400 as images. Also, data corresponding to the refractive powers of the spherical lens 91000, which has a refractive power of −S diopters, and the concave lens 92000, which has a refractive power of −C diopters, can be obtained from the amounts of movement of the projecting lens 20 and the focusing lens 320.

More specifically, FIG. 2 schematically shows the compound myopic astigmatism eye 1000 to be examined and shows the state of the light rays when the projecting lens 20 or the focusing lens 320 is located at a reference position $X_O$. As the projecting lens 210 and the focusing lens 320 are moved, an image of a circle of least confusion 1700c is formed on the eyeground. An image that corresponds to the image of the circle of least confusion 1700c is formed in the photoelectric detector 400, and its image signal is recorded in the memory means 410 together with the amount of movement of the projecting lens 210 as described above. The front-side focal line 1500 and the rear-side focal line 1600 are determined from the image signal recorded in the memory means 410. Suppose that the position of the projecting lens 210 that corresponds to one of the image signals is $X_1$, and that the position of the focusing lens 320 that corresponds to the image signal is $X_2$. Then, $|X_1-X_2|$ corresponds to astigmatic power, and $|X_1|$ corresponds to spherical power.

It should be noted that the S diopters of the spherical lens 91000 corresponds to spherical power in terms of optical aberration. If the eye 1000 to be examined has an optical aberration only with a spherical power (−S) and astigmatism (−C), the incident parallel light rays can be focused on the retina 1030 by performing the above-mentioned correction, as shown in FIG. 3. As a result, the subject examined will acquire considerably good eyesight by the above-mentioned correction if the subject examined has no disorders in the retina 1030 and other parts after the retina 1030.

Figure 4:
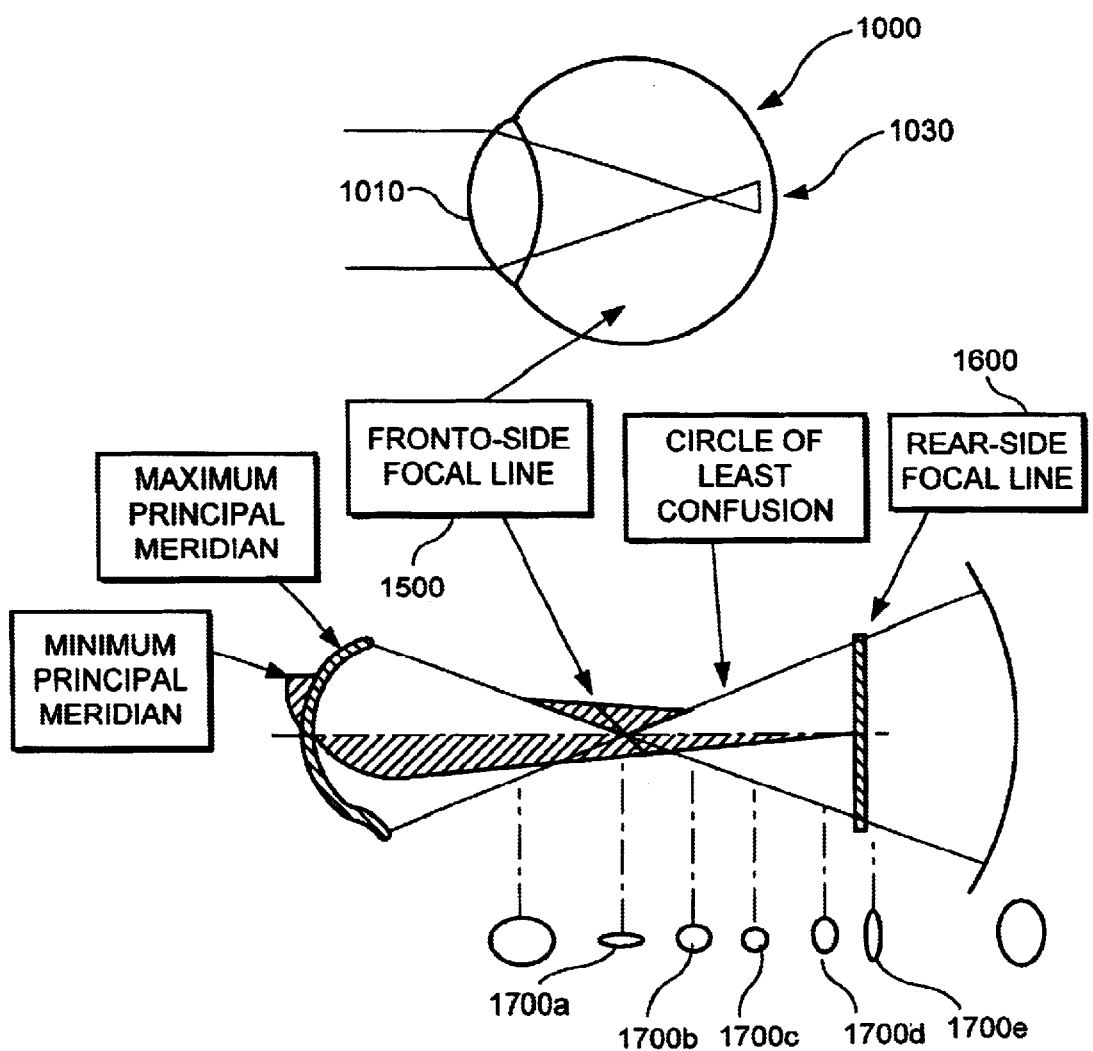
FIG. 4 is a diagram showing schematically the state of bundle of rays when an eye to be inspected includes that other than astigmatism.

In addition, as shown in FIG. 4, the eye 1000 to be examined may have factors that lower the optical performance of the eye other than spherical power (−S) and astigmatism (−C), such as spherical aberration, coma aberration, and other irregular optical aberrations, or scattering and opacity due to a cataract and the like. In this case, a front-side focal line 1500 and a rear-side focal line 1600 obtained by the above-mentioned measurement will become less clear than the front-side focal line 1500 and the rear-side focal line 1600 mentioned above.

FIGS. 5(a) to 5(d) show a front-side focal line 1500 and a rear-side focal line 1600 as light intensity distributions.

The light intensity distribution of a rear-side focal line 1600 is shown in FIG. 5(a).

$P_x=f_x(x)$ representing a section in the X direction shows the light intensity distribution in the direction in which the light rays of the rear-side focal line 1600 are most focused.

Similarly, the light intensity distribution of the front-side focal line 1500 or $P_y=f_y(y)$ representing section in the Y direction shows the light intensity distribution in the direction in which the light rays of the front-side focal line 1500 are most focused. These light intensity distributions are calculated by an arithmetic processing means including the CPU from an image signal from an image signal from the photoelectric detector 400.

Two-dimensional light intensity distribution is expressed by elliptic approximation at light intensity I (i), as shown in FIGS. 5(c) and (d).

For example, in FIG. 5(d), two-dimensional light intensity distribution is calculated as $P_{xy}=f_{xy}(f_x(x), f_y(y))$. $P_{xy}$ shows light intensity distribution on the retina 1030 of the eye 1000 that is obtained when the eye 1000 is corrected with an eyeglass lens 90000 which combines a spherical lens 91000 with a refractive power of −S diopters and a cylindrical lens 92000 with a refractive power of −C diopters.

As shown in FIG. 6, $P_{xy}$ obtained in the manner described above is combined with the optotype $O_{xy}$ that the eye being examined 1000 is actually looking at, and is then integrated to obtain an image $I_{xy}$. The image $I_{xy}$ shows an image on the retina 1030 of the eye 1000 that is obtained when the eye 1000 is corrected with the eyeglass lens 90000 which combined the spherical lens 91000 with a refractive power of −S diopters and the cylindrical lens 92000 with a refractive power of −C diopterrs. This means that the image $I_{xy}$ can be displayed means 620 as shown in FIG. 7.

It should be noted that ophthalmologic characteristics correspond to refractive powers (spherical power, astigmatic power, and astigmatic axis) and other factors such as irregular astigmatism components, scattering, and opacity.

The procedure described above makes it possible to estimate an image on the retina 1030 of the subject examined that will be actually obtained after correction with the eyeglass lens 90000, by measuring the eye 1000 to be examined with the optical characteristic measuring apparatus 9000 of the first embodiment of the present invention.

Specifically, the first embodiment of the present invention makes it possible to automatically and objectively measure accurate optical characteristics of the eye including the refractive powers (spherical power, astigmatic power, and astigmatic axis) and the irregular astigmatism components of the eye, which can be corrected with an eyeglass lens 90000. Also the first embodiment of the present invention makes it possible to, based on the result of the above measurement, display on the display means 84 an index image observed by the subject when the subject wears an appropriate eyeglass lens 90000. Thus, the examiner can easily understand in a single measurement the extent to which the eye to be examined can be corrected with an eyeglass lens 90000. In addition, according to the first embodiment of the present invention, changes in the image of the index when the refractive power of the correction lens is changed can be displayed by arithmetic without performing another measurement. Therefore, the examiner can readily perform simulation to decide the refractive power of the eyeglass lens to be prescribed to the subject examined.

In the first embodiment, description has been made with respect to compound myopic astigmatism. However, eyes with other refraction irregularities can also be measured.

In the first embodiment, an image on the retina of the eye is estimated by light intensity distribution that is obtained after correction based on information on a front-side focal line 1500 and a rear-side focal line 1600. However, it is also possible to estimate an image on the retina of the eye when an arbitrary eyeglass lens 90000 is used, by using light intensity distribution that is corrected based on information obtained from the refractive power of the arbitrary eyeglass lens 90000.

It is also possible to calculate MTF from PSF that is obtained based on information on a front-side focal line 1500 and a rear-side focal line 1600, and estimate an image on the retina of the eye when the characteristics of MTF are changed.

In the present invention constituted as above described, the projecting optical system has the light source and by bundle of rays from the light source, the measurement target is projected to the fundus of the eye to be inspected. The light receiving optical system condenses the bundle of rays reflected from the fundus of the eye, and the photoelectric detector detects the light quantity distribution characteristics of the image formed by the light receiving optical system. The arithmetic unit calculates the eye optical characteristics of the eye based on the signal output from the photoelectric detector, and the deflecting optical member for deflecting the bundle of rays being incident into both optical paths of the projecting optical system and the light receiving optical system is arranged rotatably. Thus there are excellent effects in that the operator can easily know to what degree the subject to be examined can be corrected one time by the eyeglass lens at the measurement, and that the speckle noise is averaged and the image free for the uneven light quantity can be obtained.

Also the present invention has effects in that variation of optotype image in the case of changing the degree of refractive index of the correction lens can be displayed by the calculation without performing measurement again, and that the operator can perform the simulation easily regarding what degree of refractive index in the eyeglass lens should be prescribed for the subject.

What is claimed is:

1. An eye characteristic measuring apparatus comprising:

a projecting optical system having a laser light source for projecting a measurement target to a fundus of an eye to be inspected by a bundle of rays emitted from said light source;

a light receiving optical system for condensing the bundle of rays reflected from the fundus of the eye;

a photoelectric detector for detecting light quantity distribution characteristics of an image formed by said light receiving optical system; and an arithmetic unit for calculating eye optical characteristic of the eye to be inspected based on a signal output from said photoelectric detector;

wherein a deflecting optical member for deflecting the bundle of rays being incident into both optical paths of said projecting optical system and said light receiving optical system is arranged so as to be rotatable, and thereby, a speckle noise is averaged for an imaged formed on the photoelectric detector.

2. An eye characteristic measuring apparatus as set forth in claim 1, wherein the deflecting optical member is arranged within the shared optical path for the projecting optical system and the light receiving optical system.

3. An eye characteristic measuring apparatus as set forth in claim 2, wherein the deflecting optical member is a deflection prism and is arranged rotatably about the optical axis.

4. An eye characteristic measuring apparatus as set forth in claim 1, wherein the laser light source comprises a super luminescent diode.

* * * * *